United States Patent [19]  [11] Patent Number: 4,725,387
Hirao et al.  [45] Date of Patent: Feb. 16, 1988

[54] PROCESS OF SHAPING ANHYDROUS CRYSTALS OF MALTITOL AND THE WHOLE CRYSTALLINE HYDROGENATED STARCH HYDROLYSATE MIXTURE SOLID CONTAINING THE CRYSTALS

[75] Inventors: Mamoru Hirao; Hiromi Hijiya; Toshio Miyaka, all of Okayama, Japan

[73] Assignee: Kabushiki Kaisha Hayashibara Seitbutsu Kagaku Kenkyujo, Okayama, Japan

[21] Appl. No.: 696,584

[22] Filed: Jan. 30, 1985

Related U.S. Application Data

[62] Division of Ser. No. 511,762, Jul. 7, 1983, abandoned, which is a division of Ser. No. 321,311, Nov. 13, 1981, Pat. No. 4,408,041.

[30] Foreign Application Priority Data

Feb. 12, 1981 [JP] Japan ................................. 56-19512

[51] Int. Cl.$^4$ ........................... B29B 9/08; B29B 9/12
[52] U.S. Cl. ........................................... 264/6; 264/8; 264/13; 264/14; 264/118; 264/126; 264/330; 424/48; 426/48; 426/589; 426/599; 426/658; 426/660; 426/804; 536/4.1; 536/18.6
[58] Field of Search ................... 264/13, 14, 118, 6, 264/8, 126, 330; 424/48; 426/48, 589, 599, 658, 660, 804; 536/4.1, 18.6

[56] References Cited

U.S. PATENT DOCUMENTS

| | | | |
|---|---|---|---|
| 2,987,445 | 6/1961 | Levesque | 264/118 |
| 3,341,415 | 9/1967 | Scott | 264/13 |
| 3,439,633 | 4/1969 | Pawlak et al. | 264/13 |
| 3,622,677 | 11/1971 | Short | 264/118 |
| 3,721,725 | 3/1973 | Briggs et al. | 264/14 |
| 3,741,776 | 6/1973 | Mitsuhashi et al. | 426/599 |
| 3,915,736 | 10/1975 | Oyamada | |
| 3,918,986 | 11/1975 | Hiraiwa | |
| 4,233,439 | 11/1980 | Schiweck et al. | 426/548 |
| 4,408,041 | 10/1983 | Hirao et al. | 426/589 |

FOREIGN PATENT DOCUMENTS

| | | | |
|---|---|---|---|
| 39981 | 11/1981 | European Pat. Off. | 536/4.1 |
| 1169433 | 5/1964 | Fed. Rep. of Germany | 536/4.1 |
| 51-32745 | 3/1976 | Japan | |
| 51-128441 | 8/1976 | Japan | |
| 52-47928 | 3/1977 | Japan | |
| 1377223 | 11/1974 | United Kingdom | |
| 1383724 | 12/1974 | United Kingdom | |

OTHER PUBLICATIONS

Wolfrom, M. J. et al., "Melibiotol and Maltitol", *J. Am. Chem. Soc.*, vol. 62, pp. 2553-2555, (1940).
Hodge, J. E. et al., "Useful Properties of Maltose", *Cereal Science Today*, vol. 17, No. 7, pp. 180-188, (1972).
Hidaka, Y. et al., "Maltitol Powder", Japan Kokai 74/87,619, *Chemical Abstracts*, 82:60391, 1975.
Ohno, S. et al., "X-Ray Crystal Structure of Maltitol (4-O-α-D-Glucopyranosyl-D-Glucitol)", *Carbohydrate Research*, 108, (1982), 163–171.
"Dictionary of Organic Compounds", vol. 5, Fourth Edition, pp. 2906–2907, (1965), Eyre & Spottswoode Publishers.
Hisano, K. et al., "Granulation of Maltitol", Japan, Kokai 75-59312, *Chemical Abstracts*, 83-133817, (1975).
Hiraiwa, T., "Free-Flowing Maltitol", Japan, Kokai 74-110,620, *Chemical Abstracts*, 82-171360, (1975).
Hiraiwa, T., "Coating and Granulation of Maltitol", 76-106,766, *Chemical Abstracts*, 86:3758, (1977).
Kane-Eda, J. et al., "Free-Flowing Maltitol Particles", Japan, Kokai 75-29,510, *Chemical Abstracts*, 83:81773, (1975).
Hiraiwa, T., "Maltitol Granulation", Japan, Kokai 76:113,813, *Chemical Abstracts*, 86:60544, (1977).

*Primary Examiner*—Jeffery Thurlow
*Assistant Examiner*—Leo B. Tentoni
*Attorney, Agent, or Firm*—Browdy and Neimark

[57] ABSTRACT

The present invention relates to anhydrous crystals of maltitol and the whole crystalline hydrogenated starch hydrolysate mixture solid containing the crystals, and processes for the production and use thereof.

6 Claims, 5 Drawing Figures

PROCESS OF SHAPING ANHYDROUS CRYSTALS OF MALTITOL AND THE WHOLE CRYSTALLINE HYDROGENATED STARCH HYDROLYSATE MIXTURE SOLID CONTAINING THE CRYSTALS

CROSS REFERENCE TO RELATED APPLICATIONS

The present application is a divisional application of Ser. No. 511,762, filed July 7, 1983, (now abandoned) which in turn is a divisional application of Ser. No. 321,311, filed Nov. 13, 1981, now U.S. Pat. No. 4,408,041.

FIELD OF THE INVENTION

The present invention relates to anhydrous crystals of maltitol and the whole hydrogenated starch hydrolysate mixture solid containing said crystals, and processes for the production and use thereof.

BACKGROUND OF THE INVENTION

Maltitol is, as described in Japan Patent Publication No. 13,699/72 (MITSUHASHI et al.), obtained by reduction of maltose, and has a sweetness which is close in quality to that of sucrose, and a sweetening power about 75% higher than that of sucrose.

Since maltitol is hardly absorbable and utilizable in the digestive system, and hardly fermentable by oral microorganisms, it has been used as a sweetener for low-caloric, dietary, low-cariogenic and health foods for diabetics, obese persons and those who are conscious of their health, including dental health.

However, since maltitol in dry solid form is extremely hygroscopic and deliquescent, and difficult to prepare into powder, it has usually been handled only in the form of an aqueous solution; thus, its use has been extremely restricted. For example, amorphous, substantially-anhydrous candies can be obtained by boiling down an aqueous maltitol solution at 180°–190° C., but the candies must be stored in a moisture proof vessel together with desiccant due to their high hygroscopicity and deliquescence; thus, the handling of such candies renders great difficulties.

As to the hygroscopic properties of maltitol, M. J. Wolfrom et al. have reported in *J. Am. Chem. Soc.*, Vol. 62, pp. 2553–2555 (1940), that maltitol had been obtained only in the form of an amorphous, white, hygroscopic solid; and J. E. Hodge et al. have reported in *Cereal Science Today*, Vol. 17, No. 7, pp. 180–188 (1972) that they had not yet obtained a non-hygroscopic solid form of maltitol and that maltitol could be crystallized as a hygroscopic ethanol complex.

As obvious from the above descriptions, only a highly hygroscopic maltitol solid has been hitherto known.

Recently, many attempts to reduce the high hygroscopicity of maltitol as much as possible, and also to obtain a maltitol in powder form have been reported. For example, Japan Kokai No. 477/74 (UENO, Kunio et al.) and 87,619/74 (HIDAKA, Yoshio et al.) disclose processes for the production of maltitol powder by admixing a hydrophilic polymer, such as an edible polymer, to an aqueous maltitol solution, and drying up the mixture to obtain the objective powder. Japan Kokai No. 59,312/75 (HISANO, Kazuaki et al.) discloses a process for the production of maltitol powder which comprises mixing a composition containing maltitol with a small amount of one or more members of monosaccharides or their sugar alcohol derivatives, melting the mixture by heating to anhydrous fusion form, cooling the resultant, and spray-drying and fluidizing in a moisture proof tower to obtain the objective maltitol powder. Japan Kokai No. 110,620/74 (HIRAIWA, Takashi), 24,206/75 (HIRAIWA, Takashi et al.), 25,514/75 (OYAMADA, Ko-ichiro et al.), 32,745/76 (HIRAIWA, Takashi), 106,766/76 (HIRAIWA, Takashi), 113,813/76 (HIRAIWA, Takashi), 128,441/76 (HIRAIWA, Takashi) and 47,928/77 (HIRAIWA, Takashi) disclose processes for the production of maltitol powder which comprise pulverizing maltitol solids under dried air conditions, and coating the resultant maltitol powder with other edible powders. Japan Kokai No. 29,510/75 (KANE-EDA, Jun et al.) discloses a method for preventing consolidation of powder containing maltitol wherein a powder containing maltitol is moistened with a solvent which substantially indissolves maltitol, and dried together with other sugar micro-powder under mixing conditions to apply coating on the particles of maltitol powder with the micro-powder.

All attempts have proved, however, unsuccessful because maltitol must be mixed with a large amount of other substance(s) or coated therewith, and the high hygroscopicity of maltitol cannot be eliminated thereby. In effect, the maltitol powder obtained by any of the above described processes or methods barely retains its powder form under ambient conditions, and still exhibits its high hygroscopicity; therefore, it is readily susceptible to moisture-absorption, consolidation and/or deliquescence under ambient conditions within a short time, and is not utilizable for practical uses.

SUMMARY OF THE INVENTION

The present inventors have investigated the properties of maltitol both to overcome these demerits, and to obtain anhydrous crystals of maltitol and crystalline mixture solids, which have heretofore been regarded as unattainable.

The respective wordings, "anhydrous crystals of maltitol" and "crystalline mixture solid," as used in the present specification and claims, mean substantially-non- or low-hygroscopic maltitol crystals which can be a product of anhydrous crystals of maltitol with a high purity, and a whole crystalline hydrogenated starch hydrolysate mixture solid containing, besides anhydrous crystals of maltitol, other sugar alcohols, such as sorbitol, maltotriitol and maltotetraitol.

These efforts have resulted in the finding that maltitol crystals can be obtained as follows: A liquefied starch solution with a low Dextrose Equivalent value (abbreviated as "DE" hereinafter), is subjected to the enzymatic actions of isoamylase (EC 3.2.1.68) and β-amylase (EC 3.2.1.2) to obtain a saccharified starch solution with a high maltose content, and the saccharified starch solution is then subjected to purification, concentration, crystallization and separation, obtaining a crystalline product with a maltose content of about 99% on dry solid basis (all "percentages" used hereinafter mean "percentages on dry solid basis" unless specified otherwise). Thereafter, an aqueous solution of the product is hydrogenated in the presence of Raney nickel catalyst, obtaining a maltitol solution with a high maltitol content up to about 98.5%. The maltitol solution is concentrated to 75%, and subjected to an about six-month standing from 35° to 5° C. in a soft-glass vessel to effect crystallization. Then, the crystals grown on the vessel wall are added as seed crystals to an 80% aqueous maltitol solution with the high maltitol content, and the admixture is then subjected to crystallization under gentle stirring conditions, obtaining a mascuite which is then separated into mother liquor and maltitol crystals. The crystals are washed by spraying a small amount of water, and recrystallized similarly as above after dissolution in water, obtaining maltitol crystals with a much higher purity.

DETAILED DESCRIPTION OF PREFERRED EMBODIMENTS

The physical and chemical investigations on the crystals have led to the finding that the crystals are anhydrous crystals of maltitol which have been hitherto unknown.

The physical and chemical properties of the anhydrous crystals of maltitol are as follows:

(1) Elemental analysis: C, 41.9%; H, 7.1%; and O, 51.0% (Found); C, 41.86%; H, 7.03%; and O, 51.11% (Calculated) for $C_{12}H_{24}O_{11}$ (2) Molecular weight: 344.3

(3) Melting point: 146.5°–147.0° C.

(4) Specific rotation: $[\alpha]_D^{20}$, +106.5° (0.1 g per cc water)

Figure 1:
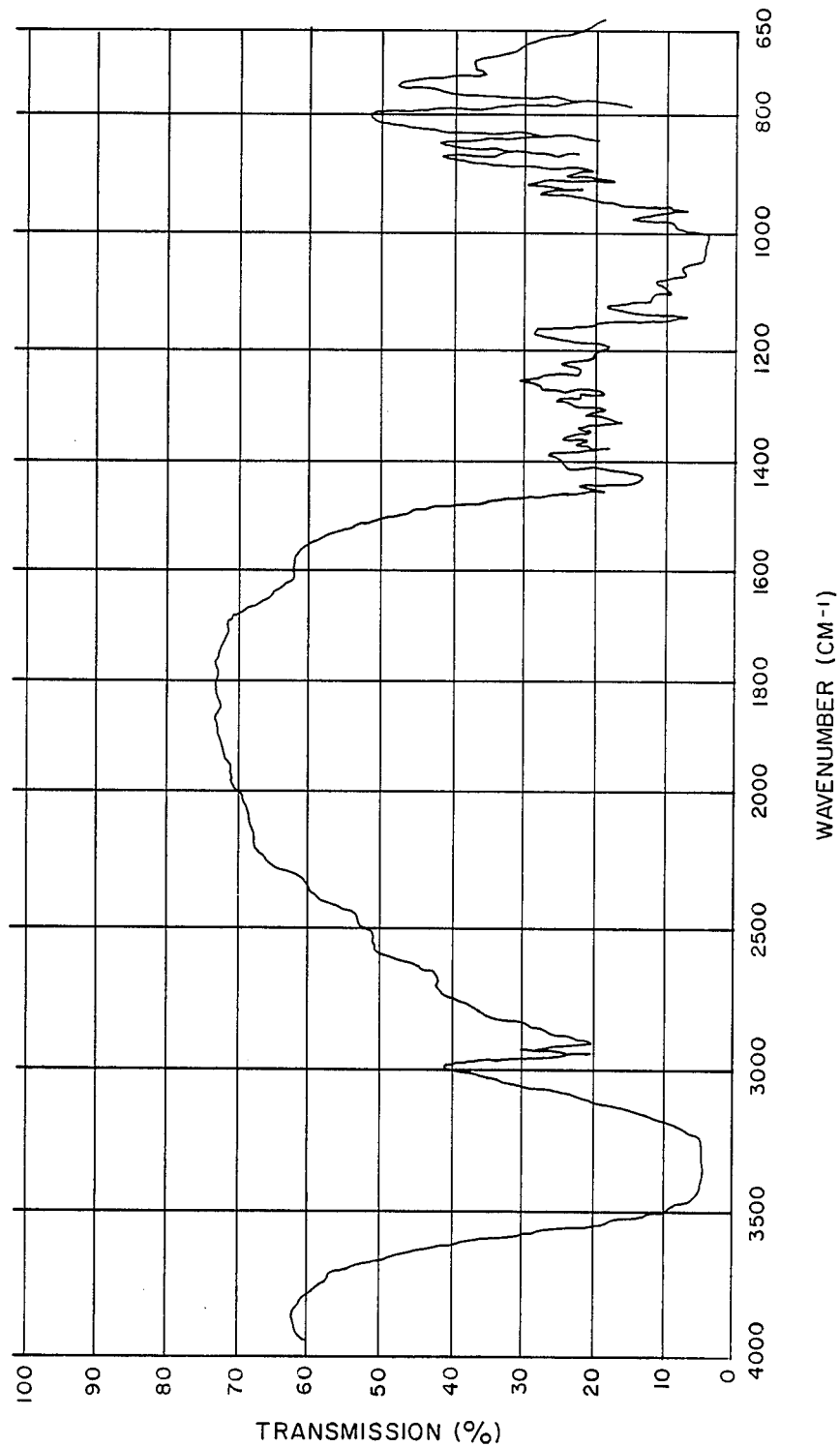
FIG. 1 is an infrared spectrum of anhydrous crystals of maltitol.
Figure 2:
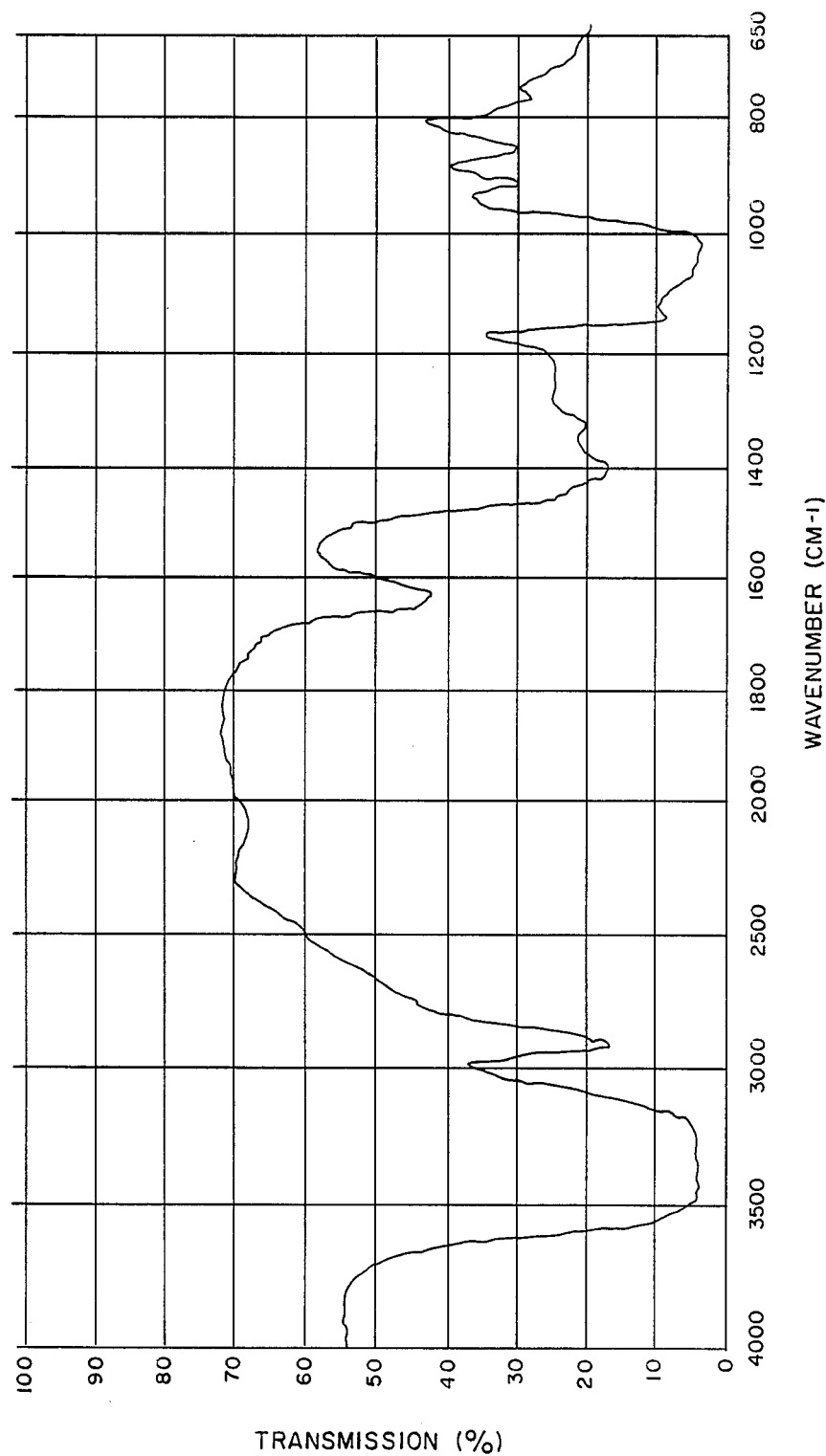
FIG. 2 is an infrared spectrum of amorphous anhydrous maltitol.

(5) Ultraviolet absorption: no characteristic absorption is observed when dissolved in water (6) Infrared absorption:
 (a) Infrared spectrum of anhydrous crystals of maltitol; 5 mg anhydrous crystals of maltitol in powder form and 220 mg KBr were mixed, and pressed into a transparent tablet, about 0.6 mm thick, which was then subjected to infrared spectrometry (FIG. 1)
 (b) Infrared spectrum of amorphous, anhydrous maltitol; 3 mg anhydrous crystals of maltitol and 220 mg KBr were dissolved in hot water, and the mixture was dried, and pressed into a transparent tablet, about 0.8 mm thick, which was then subjected to infrared spectrometry (FIG. 2)

(7) Solubility: 100 g water dissolves up to 165 g anhydrous crystals of maltitol at 25° C.

Figure 3:
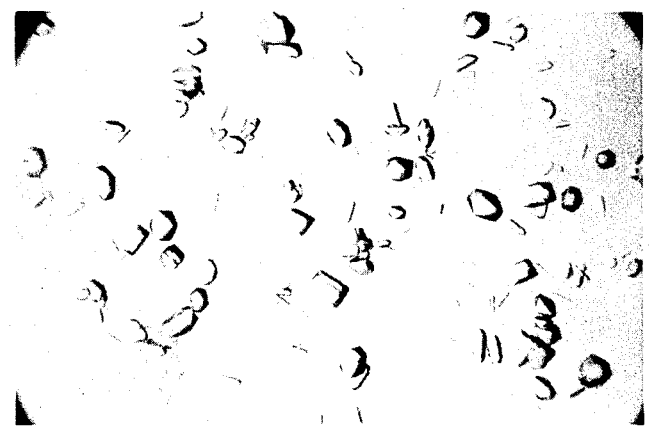
FIG. 3 is a microphotograph of anhydrous crystals of maltitol, ×150.
Figure 4:
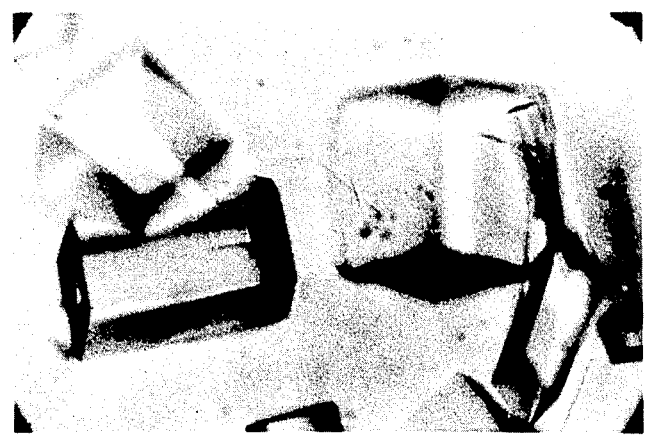
FIG. 4 is a microphotograph of anhydrous crystals of maltitol, ×600.

(8) Heat of dissolution: upon dissolution of 1 mole anhydrous crystals of maltitol in 190 mole water at 15° C., 5.5 Kcal is endothermically absorbed (9) Appearances and properties: colorless, odorless, transparent crystals (micro-crystals in lump white); no hygroscopicity and deliquescence are observed; weight reduction upon heating at 130° C. for two hours is 0.5% or less; an aqueous solution of anhydrous crystals of maltitol is neutral or weakly acidic; and sweet tasting. FIGS. 3 and 4 are microphotographs of anhydrous crystals of maltitol grown from an aqueous maltitol solution.

(10) Solubility in various solvents: readily soluble in water, 0.1N NaOH and 0.1N HCl; soluble in methanol and ethanol; and insoluble in chloroform and ethyl acetate

(11) Color reaction: anthrone-sulfuric acid reaction, green; Fehling reduction reaction, negative; and $I_2$-test, negative

(12) Sugar components:
 (a) Acid hydrolysis using 1N sulfuric acid, and subsequent paper and gas-liquid chromtographic analyses confirmed the presence of equimolar D-glucose and D-sorbitol fractions
 (b) Complete methylation, hydrolysis and subsequent gas-liquid chromatographic analysis confirmed the presence of equimolar 2,3,4,6-tetra-O-methyl-D-glucose aND 1,2,3,5,6-penta-O-methyl-D-sorbitol fractions
 (c) The high specific rotation, $[\alpha]_D^{20}$, of +106.5° and the infrared absorption neighboring 840 $cm^{-1}$ suggest the presence of an α-linkage between the glucose and sorbitol moieties
 (d) Paper, gas-liquid and high-pressure liquid chromatographic analyses on the anhydrous crystals of maltitol gave the same single spot or peak at the same position as in the analyses on a commercial authentic maltitol preparation (special grade reagent)

Figure 5:
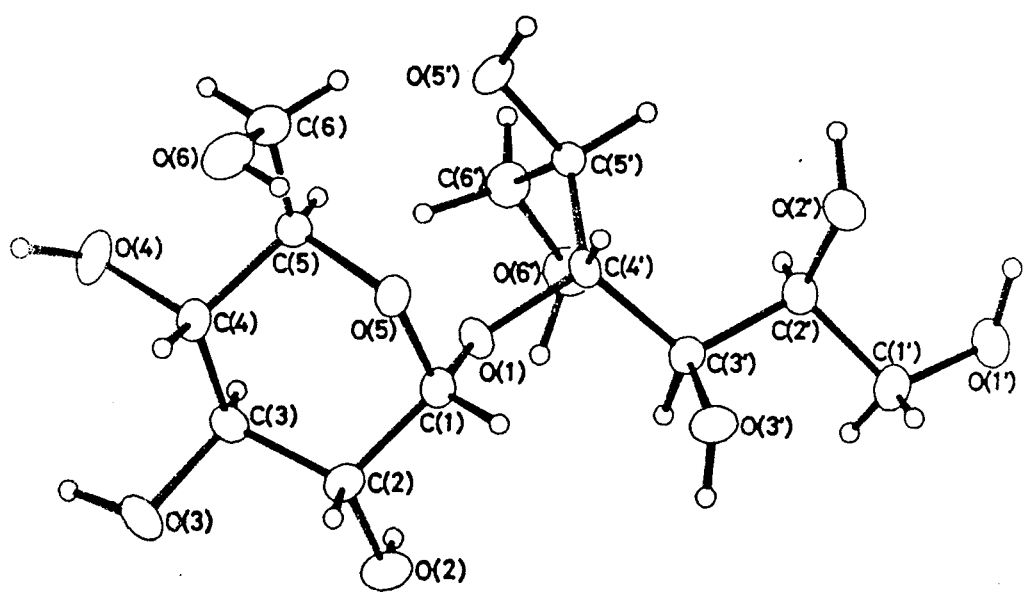
FIG. 5 is a stereo-scopic ORTEP figure of maltitol single crystal.

(13) X-ray crystal structure: X-ray crystallographic study on a maltitol single crystal grown from a 75 w/w % supersaturated aqueous maltitol solution at 40° C. gave the following crystal structure; orthorhombic, space group, $P2_12_12_1$; lattice constants, a=8.166 Å, b=12.721 Å, c=13.629 Å; and a stereoscopic ORTEP figure is given in FIG. 5.

The above-described physical and chemical properties of the maltitol crystals led to the conclusion that the present crystals are hitherto unknown anhydrous crystals of maltitol neither sugar hydrate, such as β-maltose mono-hydrate, nor the reported ethanol complex.

The following descriptions illustrate the process for the production of anhydrous crystals of maltitol and crystalline mixture solid according to the present invention.

As to the maltitol solution which is subjected to crystallization according to the present invention, any maltitol solution can be used regardless of its production process so far as anhydrous crystals of maltitol can grow from the solution by the addition of seed crystals at a supersaturated concentration. Usually, an aqueous maltitol solution, prepared with a sugar alcohol mixture having a maltitol content at least 65% to give a concentration, preferably, of 65-95% (supersaturation degree of about 1.05-1.50), is subjected to crystallization at a temperature in the range of 0°-95° C., a range wherein freezing of the solution does not occur, and wherein the heat loss is relatively low.

The supersaturation degree and viscosity of the solution can be regulated by the addition of water-soluble organic solvent, e.g., methanol, ethanol or acetone.

Crystallization of the solution is usually started in a crystallizer at a relatively elevated temperature of about 40°-95° C. and a supersaturated concentration, and the content is simultaneously cooled gradually with gentle stirring down from the temperature to obtain a mascuite containing anhydrous crystals of maltitol. In this case, the presence of seed crystals in an amount of 0.1-20.0% can accelerate the crystallization.

As described above, anhydrous crystals of maltitol can be easily crystallized from a supersaturated aqueous maltitol solution by adding thereto a small amount of anhydrous crystals of maltitol or crystalline mixture solid as seed crystals.

The mascuite thus obtained can be separated into the anhydrous crystals of maltitol and mother liquor by conventional separation method, or prepared into a crystalline mixture solid by a conventional total-sugar method such as block-pulverization, fluidized-bed granulation and spray-drying methods.

The former method usually comprises transferring the mascuite into a basket-type centrifugator, separating the mascuite into anhydrous crystals of maltitol and mother liquor, and washing, if necessary, by spraying a small amount of chilled water thereto, obtaining anhydrous crystals of maltitol with a much higher purity.

The total-sugar method does not augment the purity of maltitol, but realizes a higher yield of crystalline mixture solid: thus, CRYSTALLINE MIXTURE SOLID obtained by any of the three methods inevitably contains, besides anhydrous crystals of maltitol, other sugar alcohols resulting from the starting material starch syrup as syrup constituents, such as sorbitol, maltotriitol and maltotetraitol.

In spray-drying, a mascuite with a concentration of about 70–85%, wherein the crystallization has proceeded up to about 25–60%, is spray-dried via a nozzle, equipped at the top of a spray-drying tower, by a high-pressure pump at a temperature whereat the obtained crystalline powder does not melt, and which is maintained, for example, by charging a 60°–100° C. hot air. Thereafter, the crystalline powder is aged by supplying a 30°–60° C. air for about one to twenty hours to obtain a non- or substantially-non-hygroscopic crystalline mixture solid.

The block-pulverization method usually comprises 0.5–5 day standing of a mascuite with a moisture content of about 5–15%, wherein the crystallization has proceeded up to about 10–60%, to solidify into blocks which are then converted into powder by scraping, pulverizing and subsequently drying.

In the latter total-sugar method, to a supersaturated solution in fusion form, prepared by concentration of an aqueous maltitol solution to a moisture content less than 5% by heating according to a conventional method, can be added seed crystals, and the admixture is then kneaded at a temperature below its melting point, obtaining crystalline mixture solid, followed by shaping of the resultant into a desirable shape, e.g., in the form of powder, granule, rod, plate or cube.

Although, dependent upon purity, the hygroscopicity of anhydrous crystals of maltitol or crystalline mixture solid slightly varies, they are substantially non-hygroscopic and free flowing; thus, they are favorable for various uses, e.g., for producing foods, drinks, cosmetics, drugs and chemical materials, or preparing into desirable shapes, similar to granulated sucrose, without fear of sticking and consolidation. Also, the physical properties of anhydrous crystals of maltitol and crystalline mixture solid, such as melting point and specific rotation, vary according to their purities; with a decrease of the purity, the melting point declines and widens its range. For example, the melting point of crystalline mixture solid with a maltitol content of 85.2% is 120°–127° C. Accordingly, the purity of both products can be selected freely to meet to the final uses.

Additionally, since like sucrose anhydrous crystals of maltitol and crystalline mixture solid dissolve readily in the mouth, and endothermically absorb more heat, they exhibit a pleasant refreshing taste; thus, they are desirable sweeteners.

Although anhydrous crystals of maltitol and crystalline mixture solid dissolve readily and quickly in water, they are substantially non-hygroscopic; thus, they are favorably feasible for sweetening powdered foods and drinks as described hereinafter.

Based on the above described features, the use of anhydrous crystals of maltitol or crystalline mixture solid easily enables industrial-scale production of various foods and drinks, such as sweeteners in powder or solid form, fondant, chocolate, chewing gum, powdered juice or convenience soup; and shaped bodies, such as granules or tablets, which have been impossible or very difficult to prepare with conventional maltitol. Furthermore, since anhydrous crystals of maltitol and crystalline mixture solid are free flowing due to their non-hygroscopicity and lowsusceptibility to consolidation, the economics realized by the reduction in labor, packing, transportation and storage costs therewith is beyond calculation.

Anhydrous crystals of maltitol and crystalline mixture solid are readily soluble in water, satisfactorily heat- and acid-resistant, low-caloric, low-cariogenic and low-fermentable, and impart an appropriate sweetness, viscosity, body and gloss to foods and drinks, similar to conventional maltitol; thus, their superior properties make the production of foods, drinks, drugs and cosmetics more feasible.

The following descriptions explain the present invention in more detail.

Anhydrous crystals of maltitol and crystalline mixture solid can be used as a sweetener without further processings, or, if necessary, in combination with other conventional sweeteners, e.g., starch syrup solid, glucose, maltose, isomerized sugar, sucrose, honey, maple sugar, sorbitol, dihydrocharcone, stevioside, α-glycosyl stevioside, sweet extract from *Momordica grosvenori*, glycyrrhizin, L-asparatyl phenylalanine methyl ester, saccharin, glycine and/or alanine; and/or in combination with fillers, e.g., dextrin, starch and/or lactose.

Also, they can be used intact, or mixed, if necessary with filler, vehicle and/or binder, and then prepared into a desirable shape, e.g., granule, globe, tablet, rod, plate or cube.

Since like conventional maltitol, they are hardly absorbable and utilizable by the digestive system, a sufficient calorie-reduction of foods and drinks can be realized therewith without changing their desirable properties; thus, they are favorably usable as a low-caloric sweetener, and for sweetening low-caloric foods and drinks, e.g., dietary and health foods, for diabetics, obese persons and those whose calorie-intakes are restricted.

Furthermore, since both products are hardly fermentable by dental caries-causative microorganisms, similarly as conventional maltitol, they can also be favorably used as a low-cariogenic sweetener for various confectionaries, e.g., chewing gum, chocolate, biscuit, cookie, caramel and candy; and soft drinks, e.g., cola drinks, cider, juice, coffee and yoghurt drinks. Also, they are favorably usable for reducing the cariogenicities of cosmetics and drugs, such as gargle and toothpaste, by replacing sucrose therewith, as well as for sweetening them.

The sweetness of anhydrous crystals of maltitol or crystalline mixture solid well harmonizes with sour, salty, astringent, delicious and/or bitter tasting substance(s) as well as being highly acid- and heat-resistant; thus, in addition to the above described special uses, they are also favorably usable for sweetening foods and drinks in general, and improving their taste qualities. For example, they may be used in seasonings such as sauce, soy sauce, soy sauce powder, soy sauce paste "MISO", soy sauce paste powder, mayonnaise, dressing, vinegar, vinegar powder, extracts for Chinese-style foods, catsup, curry roux, extracts for stew and soup, mixed seasonings and table and coffee sugars; confectionaries and bakery products such as Japanese-style confectionaries, jelly, castella, bread, biscuit, cracker, cookie, pie, pudding, butter cream, custard cream, choux cream, cream puff, waffle, sponge cake, doughnut, chocolate, chewing gum, caramel and candy; frozen desserts such as ice-cream and sherbert; syrups; pastes such as peanut paste, flour paste and fruit paste; pickles and preserves such as jam, marmalade, preserves, processed vegetable and pickles; pickle additives; meat products such as ham and sausage; processed fish products such as ham and sausage; preserved foods; daily products such as cooked beans and potato salad; canned and bottled foods such as those of fish, meat, fruit, vegetable and shell; alcoholic drinks such as wine, whisky and brandy; soft drinks such as coffee, cocoa, juice, carbonate drinks, lactic acid drinks and yoghurt drinks; and convenience-type foods and drinks such as those of pudding, hot cake, juice, coffee and soup.

Anhydrous crystals of maltitol and crystalline mixture solid are non-hygroscopic and free flowing; thus, they are favorably usable for improving the properties of pre-packed foods, and/or preventing the sticking and adhesion of the content on the package, for example, as in the case of chewing gum.

Additionally, they are favorably feasible for improving the tastes of pet foods or feeds for domestic animal or fowl, honey bee, silkworm or fish, as well as for sweetening and improving the tastes of tobacco, cosmetics and drugs which are in the form of solid, liquid or paste, such as toothpaste, lipstick, lipcream, drug for internal administration, troche, cod-liver oil drop, cachou, gargle and oral refreshing agent.

Anhydrous crystals of maltitol and crystalline mixture solid obtained according to the present invention can be prepared into any desirable shape by spraying a small amount of water or an aqueous maltitol solution thereon to slightly moisten them, and molding the resultant under a slightly elevated pressure, as in the case of sucrose; for example, in the shape of fish, animal, cube or flower. Thus, shaped sweetener for coffee or tea in any desirable shape can be easily prepared to meet to the final uses. To the shaped sweetener can be added other sweeteners, e.g., α-glycosyl stevioside, sucrose and/or saccharin to further enhance the sweetness; caloring agent, for example, red or green; and/or flavor such as orange-, coffee- or brandy flavor. In flavoring, the objectives may be attainable with the use of a flavor-cyclodextrin complex (a host-guest complex).

Furthermore, since like sucrose they can be easily obtained in massive form, they are flavoring usable as a semi- or transparent sweetener solid in place of the conventional candy sugar or coffee sugar.

Additionally, to anhydrous crystals of maltitol or crystalline mixture solid can be added freely other substance(s), e.g., vitamin, antibiotics or microorganisms of genus Lactobacillus, prior to shaping, and the admixture is then prepared into desirable shape, for example, granule with a granulizer, or tablet with a tabletting machine.

As to the methods for incorporating anhydrous crystals of maltitol or crystalline mixture solid into the above described foods, drinks, tabocco, pet foods, feeds, cosmetics, drugs or shaped bodies, any methods can be employed in the invention so far as they are incorporated therein before the completion of processing. Preferable conventional methods are mixing, kneading, dissolving, dipping, melting, immersing, permeating, injecting, crystallizing and solidifying.

In addition to the above described uses, anhydrous crystals of maltitol and crystalline mixture solid are of low-moisture content or substantially anhydrous, and the small amount of moisture present therein can be removed completely by brief drying with hot air; thus, they can be favorably used in chemical reaction under anhydrous conditions. For example, etherification or esterification reaction of anhydrous crystals of maltitol or crystalline mixture solid under anhydrous conditions leads to a higher yield of ether or ester derivative of maltitol. The derivatives thus obtained can be favorably used, for example, as an emulsifier or surface-active agent.

Several embodiments of the present invention are disclosed hereinafter.

EXAMPLE 1

Seed Crystal

To a starch suspension, consisting of one part of potato starch and ten parts of water, was added a commercial liquefying α-amylase, and the mixture was heated to 90° C. to effect gelatinization. The enzymatic liquefaction was suspended by immediately heating to 130° C., obtaining a liquefied starch solution with DE of about 0.5.

After cooling immediately the solution to 55° C., to the solution was added *Pseudomonas amyloderamosa* (ATCC 21262) isoamylase (EC 3.2.1.68) in an amount of 100 units per g starch, and a soy bean ⊕-amylase "#1500" (Nagase & Company, Ltd., Osaka, Japan) in an amount of 50 units per g starch, and the mixture was saccharified at this temperature and pH 5.0 for 40 hours, obtaining a saccharified starch solution with a high maltose content: glucose, 0.4%; maltose, 92.5%; maltotriose, 5.0%; and higher oligosaccharides including maltotetraose, 2.1%.

The saccharified starch solution was purified by decolorization with activated carbon, and deionization with ion exchangers.

After concentrating the purified saccharified starch solution of 75%, the concetrate was transferred into a crystallizer, and β-maltose mono-hydrate was added thereto as seed crystals in an amount of 1%. The resultant admixture was then cooled gradually from 40° C. to 30° C. over a period of two days, followed by separation of the resultant mascuite with a basket-type centrifugator into crystalline maltose and mother liquor. The crystalline maltose was washed by spraying with a small amount of water, obtaining a highly-purified maltose with a purity of 99.0%.

A 50% aqueous solution of the highly-purified maltose was placed in an autoclave, and added with Raney nickel catalyst in an amount of 10%. Thereafter, the content was heated to 90°–125° C., and hydrogenation was effected at the temperature and a hydrogen pressure of 20–100 kg/cm$^2$. After completion of the hydrogenation, the Raney nickel catalyst was removed, and the residual aqueous solution was purified by decolorization with activated carbon, and deionization with ion exchangers according to conventional methods, obtaining a highly-purified maltitol solution with a purity of 98.5%.

After concentrating the highly-purified maltitol solution to 75% under a reduced pressure, a small portion of the concentrate was placed in a soft-glass vessel, and allowed to stand at 30°–5° C. for about six months to effect crystallization, resulting in the growth of the anhydrous crystals of maltitol on the vessel wall.

To an 80% aqueous maltitol solution was added the anhydrous crystals of maltitol as seed crystals, and the mixture was crystallized under gentle stirring conditions. The resultant mascuite was then transferred into a basket-type centrifugator, and separated therein into crystals and mother liquor. The crystals were then washed by spraying with a small amount of water, obtaining a highly-purified anhydrous crystals of maltitol with a purity of 99.8%.

The anhydrous crystals of maltitol have the following physical properties: melting point, 146.5°–147.0° C.; 100 g water dissolves up to 165 g anhydrous crystals of maltitol at 25° C.; and no hygroscopicity is observed under ambient conditions.

The anhydrous crystals of maltitol are favorably usable as seed crystals in the production of additional anhydrous crystals of maltitol or crystalline mixture solid.

EXAMPLE 2

Anhydrous Crystals of Maltitol

To a starch suspension, consisting of one part of potato starch and ten parts of water, was added a commercial Bacillus liquefying α-amylase, and the mixture was then heated to 90° C. to effect gelatinization. The enzymatic liquefaction was suspended immediately by heating the mixture to 130° C., obtaining a liquefied starch solution with a DE of about 0.5. The solution was then immediately cooled to 50° C., and added with an *Escherichia intermedia* (ATCC 21073) pullulanase (EC 3.2.1.41) in an amount of 50 units per g starch, and a soy bean β-amylase "#1500" (Nagase & Company, Ltd., Osaka, Japan) in an amount of 30 units per g starch. The enzymatic saccharification was continued at this temperature and pH 6.0 for 46 hours, and the saccharified starch solution was decolorized with activated carbon, and subsequently deionized with ion exchangers, obtaining a maltose solution with a sugar composition of glucose, 0.4%, maltose, 92.5%, maltotriose, 4.8%, and higher oligosaccharides including maltotetraose, 2.3%, in the yield of about 97% against the starting starch material.

After adjusting the concentration of the maltose solution to 50%, to the concentrate was added Raney nickel catalyst in an amount of 10%, and the admixture was then heated to 90°–125° C. under stirring conditions, and hydrogenated at this temperature under a hydrogen pressure of 20–100 kg/cm$^2$. After completion of the hydrogenation, the Raney nickel catalyst was removed, and the hydrogenated product was purified with activated carbon and ion exchangers according to conventional methods, obtaining a sugar alcohol mixture with a composition of sorbitol, 0.8%, maltitol, 92.2%, maltotriitol, 4.6%, and higher sugar alcohols including maltotetraitol, 2.4%, in the yield of about 92% against the starting starch material.

After concentrating the mixture to 80%, the concentrate was then transferred into a crystallizer, added with anhydrous crystals of maltitol in powder form as seed crystals in an amount of 1%, and cooled gradually from 50° C. to 20° C. over a period of three days under stirring conditions. The resultant mascuite was separated with a basket-type centrifugator into crystals and mother liquor. The crystals were washed by spraying with a small amount of water, obtaining the titled product with a maltitol content of 99.2% in the yield of about 46% against the starting starch material.

The melting point of the product was 146.5°–147.0° C.

The product is highly pure and non-hygroscopic; thus, it is favorably usable as a chemical material as well as sweetener and/or taste-improving agent for various foods, drinks, cosmetics and drugs.

EXAMPLE 3

Crystalline Mixture Solid

To a starch suspension, consisting of three parts of corn starch and ten parts of water, was added a commercial Bacillus liquefying α-amylase, and the mixture was heated to 90° C. to effect gelatinization. The enzymatic liquefaction was suspended by heating immediately the mixture to 130° C., obtaining a liquefied starch solution with a DE of about 3.

After cooling immediately the solution to 55° C., to the solution was added *Pseudomonas amyloderamosa* (ATCC 21262) isoamylase (EC 3.2.1.68) in an amount of 100 units per g starch, and a soy bean β-amylase "#1500" (Nagase & Company, Ltd., Osaka, Japan) in an amount of 30 units per g starch, and the mixture was kept at this temperature and pH 5.0 for 36 hours to effect enzymatic saccharification. The saccharified starch solution was purified similarly as in EXAMPLE 2, obtaining a maltose solution with a sugar composition of glucose, 2.6%, maltose, 85.4%, maltotriose, 7.4%, and higher oligosaccharides including maltotetraose, 4.6%.

Then, the hydrogenation of the maltose solution was carried out similarly as in EXAMPLE 2, obtaining a sugar alcohol mixture with a composition of sorbitol, 3.6%, maltitol, 85.4%, maltotriitol, 6.8%, and higher sugar alcohols including maltotetraitol, 4.6%.

Thereafter, the mixture was concentrated to 88%, and the concentrate was transferred into a crystallizer, added with anhydrous crystals of maltitol in powder form as seed crystals in an amount of 2%, and kept at 50° C. for two hours under gentle stirring conditions. The content was then placed in plastic vessels where it was allowed to stand at 20° C. for 4 days to effect solidification. The obtained blocks were removed from the vessels, and pulverized by a crusher equipped with a scraper. The resultant was dried to obtain the titled product in the yield of 90% against the starting starch material.

The melting point of the product is 120°–127° C.

The product is substantially non-hygroscopic and readily handleable: thus, it is favorably usable for improving the tastes of various foods, drinks, cosmetics and drugs as well as sweetening them.

EXAMPLE 4

Crystalline Mixture Solid

After concentrating a sugar alcohol mixture, obtained similarly as in EXAMPLE 2, to 80%, the concentrate was then transferred into a crystallizer, and added with crystalline mixture solid in powder form as seed crystals in an amount of 2%. The admixture was cooled gradually from 50° C. with gentle stirring, obtaining a mascuite wherein the crystallization had proceeded up to 35%. The mascuite was then spray-dried via a 1.5 mm$\phi$ nozzle, equipped at the top of a spraying tower, with a high-pressure pump at a pressure of 150 kg/cm$^2$. Simultaneously, an 85° C. hot air was charged downwards from the top of the tower to collect the pulverized product on a net conveyer placed at the bottom of the tower, and to fluidize the product out of the tower over a period of 40 minutes while charging a 40° C. air upwards through the net. The resultant was then transferred into an aging tower, and aged therein for ten hours to effect complete crystallization and drying, obtaining the titled product in the yield of about 92% against the starting starch material.

The product is non-hygroscopic and readily handleable; thus, it is favorably usable in various chemical materials as well as in sweeteners.

EXAMPLE 5

Fondant

A starch suspension, consisting of five parts of corn starch and ten parts of water, was liquefied similarly as in EXAMPLE 3, obtaining a liquefied starch solution with DE of 5.

After cooling immediately the solution to 55° C., to the solution was added the isoamylase in an amount of 70 units per g starch and the $\beta$-amylase in an amount of 10 units per g starch, and the mixture was kept at this temperature and pH 5.0 for 36 hours to effect enzymatic saccharification. The resultant was then purified similarly as in EXAMPLE 2 to obtain a saccharified starch solution with a sugar composition of glucose, 0.9%, maltose, 77.6%, maltotriose, 12.5%, and higher oligosaccharides including maltotetraose, 9.0%.

The solution was then hydrogenated similarly as in EXAMPLE 2, obtaining a sugar alcohol mixture with a composition of sorbitol, 1.4%, maltitol, 77.3%, maltotriitol, 12.3%, and higher sugar alcohols including maltotetraitol, 9.0%.

After concentration of the mixture to 85%, the concentrate was transferred into a crystallizer, added with seed crystals in an amount of 1%, and then cooled to ambient temperature under vigorous stirring conditions to effect crystallization. To the resultant was admixed anhydrous crystals of maltitol obtained similarly as in EXAMPLE 2, to obtain the titled product.

The product is a white paste with a smooth and mild sweetness; thus, it is favorably usable as a material for various confectionaries.

EXAMPLE 6

Sweetener

A mixed sweetener was prepared by mixing homogenously one part of crystalline mixture solid in powder form, obtained similarly as in EXAMPLE 3, and 0.05 parts of a commercial $\alpha$-glycosyl stevioside "$\alpha$-G-Sweet" (Toyo Sugar Refining Co., Ltd., Tokyo, Japan).

The mixed sweetener has an excellent sweetness which is about two-fold higher in sweetening power than that of sucrose, but the calorie-content is about one-twentieth of that of sucrose; thus, the sweetener is favorably usable for various low-caloric foods and drinks for diabetics, obese persons and those whose calorie-intakes are restricted. Additionally, since neither acid- nor water insoluble glucan formation by dental caries causative-microorganisms is observed, it is favorably usable for sweetening various low-cariogenic foods and drinks.

EXAMPLE 7

Cube Maltitol

One part of anhydrous crystals of maltitol, obtained similarly as in EXAMPLE 2, and 0.01 part of saccharin were mixed to homogeneity. After moistening the mixture by spraying thereonto a small amount of an aqueous maltitol solution, the resultant was formed into cubes using molds for conventional cubic sugar under a relatively elevated pressure, and the cubes were removed from the molds, obtaining the titled product.

The product is a white, non-hygroscopic cube with sufficient physical strength and about two-fold higher sweetening power in comparison with that of sucrose as well as being readily soluble in cold water; thus, it is an ideal low-caloric and low-cariogenic sweetener.

EXAMPLE 8

Cream Wafers

A creamy product, prepared by mechanical mixing of a mixture consisting of 2,000 parts of crystalline mixture solid in powder form, obtained similarly as in EXAMPLE 3, 1,000 parts of shortening, one part of lecithin, one part of lemon oil and one part of vanilla oil, according to conventional methods, was kept at 40°-45° C., and sandwiched between wafers to obtain the titled product.

EXAMPLE 9

Custard Cream

Five hundred parts of corn starch, 500 parts of crystalline mixture solid in powder form, obtained similarly as in EXAMPLE 4, 400 parts of maltose and 5 parts of NaCl were sufficiently mixed by shifting and sieving, and the mixture was added with 1,400 parts of egg, followed by stirring. Then, the mixture was gradually added with 5,000 parts of boiling milk while stirring and heating the content on a slow-fire, and the heating was suspended when the corn starch gelatinized and the content became transparent. Then, to the cooled content was further added a small amount of vanilla flavor to obtain the titled product.

The product is a smooth, glossy and very delicious custard cream with no excessive sweetness.

EXAMPLE 10

Chocolate

A mixture, consisting of 40 parts of cacao base, 10 parts of cacao butter and 50 parts of anhydrous crystals of maltitol, obtained similarly as in EXAMPLE 2, was placed in a refiner to reduce its viscosity. Then, the content was transferred into a conche, and kneaded sufficiently therein at 50° C. for two days.

During the kneading step, 0.5 parts of lecithin was added thereto and dispersed sufficiently.

Thereafter, the content was charged at 30° C. under thermally-regulated conditions into molds just before its solidification. The content was degassed by vibration, and solidified by passing through a 10° C. cooling tunnel for 20 minutes. The contents were then removed, and packed to obtain the titled product.

The product is a non-hygroscopic chocolate with a mild and elegant favor, excellent color and satisfactory brightness and texture, and melts smoothly in the mouth; thus, it is an ideal low-cariogenic and low-caloric chocolate.

EXAMPLE 11

Chocolate Coated Candy

A mixture, consisting of 95 parts of crystalline mixture solid in powder form, obtained similarly as in EXAMPLE 3, 5 parts of corn syrup and a small amount of water, was homogenized by stirring to fluid state. Then, to the mixture was added small amounts of flavor and coloring agent, and the admixture was poured with a depositor into molds in layered starch, and solidified partially therein. The flour starch attached thereon was removed by shifting and sieving to obtain the centers for the titled product. The centers were coated with an unsolidified chocolate, obtained similarly as in EXAMPLE 10, cooled, solidified, and finally packed to obtain the titled product.

EXAMPLE 12

Chewing Gum

Twenty-five parts of gum base and 40 parts of a fondant, obtained similarly as in EXAMPLE 5, were kneaded at 60° C. by a mechanical mixer. To the mixture was added 30 parts of anhydrous crystals of maltitole, obtained similarly as in EXAMPLE 2, 1.5 parts of calcium phosphate, 0.1 part of L-menthol-$\beta$-cyclodextrin complex (a host-guest complex), and small amounts of condiments, and the admixture was then kneaded sufficiently, rolled and cut according to conventional methods to obtain the titled product.

The product is an ideal low-cariogenic chewing gum.

EXAMPLE 13

Juice Powder

Thirty-eight parts of juice powder, obtained by spraydrying, was added with 60 parts of crystalline mixture solid in powder form, obtained similarly as in EXAMPLE 4, 0.65 parts of citric anhydride, 0.1 part of malic acid, 0.1 part of ascorbic acid, 0.1 part of sodium citrate, 0.6 parts of a favor powder and 0.5 parts of pullulan, and the mixture was kneaded sufficiently.

Then, the mixture was granulated in a fluidized-bed granulizer wherein the mixture was first moistened by spraying thereon a 50% aqueous maltitol solution, obtained similarly as in EXAMPLE 3, at a rate of 100 ml per minute, and then fluidized into powder over a period of 30 minutes by charging a 40° C. air at a rate of 150 $m^3$ per minute.

The product thus obtained is a powdered juice with a powder orange juice content of about 30%, and is free from unpleasant odor and taste as well as being stable over the long period of storage without consolidation.

EXAMPLE 14

Convenience Potage Soup

A mixture, consisting of 30 parts of gelatinized corn powder, 5 parts of gelatinized wheat flour, 4 parts of gelatinized potato starch, 12 parts of gelatinized waxy corn starch, 8 parts of crystalline mixture solid in powder form, obtained similarly as in EXAMPLE 3, 5 parts of sodium glutamate, 8.5 parts of NaCl, 7 parts of defatted mild and 0.5 parts of onion powder, was crushed and mixed sufficiently. The mixture was then further added with 0.5 parts of a melted sorbitan aliphatic acid ester, 9 parts of a melted hydrogenated vegetable oil and 10 parts of lactose, and the admixture was mixed sufficiently.

The admixture was granulated similarly as in Example 13 in a fluidized-bed granulizer wherein the admixture was sprayed with a small amount of water, fluidized, and dried by a 70° C. hot air. Thereafter, the resultant was shifted and sieved to obtain the titled product.

An addition of hot water to the product readily dissolves and disperses the product to give instantly a potage soup with an excellent flavor.

EXAMPLE 15

Extract of "UIRO"

A mixture, consisting of 90 parts of rice flour, 20 parts of corn starch, 120 parts of crystalline mixture solid in powder form, obtained similarly as in EXAMPLE 4, and 4 parts of pullulan, was kneaded to homogeneity to obtain the titled product, "Extract of UIRO"—a type of Japanese-style rice paste confectionaries.

Two hundred g of the extract and 1 g green tea powder ("MACCHA") were added with water, and the mixture was kneaded sufficiently. Then, the resultant was placed in a vessel, and steamed therein for 60 minutes to obtain a "MACCHA UIRO".

The product is excellent in gloss, flavor and biting properties. Also, the retrogradation of the amylaceous components is sufficiently suppressed, and therefore the product is stable over a long period of storage.

EXAMPLE 16

Pickle Additive for "BETTARA-ZUKE"

Four parts of crystalline mixture solid in powder form, obtained similarly as in EXAMPLE 3, 0.05 parts of sweet extract from Licorice, 0.008 parts of malic acid, 0.07 parts of sodium glutamate, 0.03 parts of potassium sorbate and 0.2 parts of pullulan were mixed and kneaded to homogeneity, obtaining the titled "Pickle additive for BETTARA-ZUKE"—a type of Japanese-style pickles.

According to conventional methods, 30 kg of Japanese radish ("DAIKON", Raphanus sativus) was partially pickled with NaCl, and then further pickled with sucrose. The final pickling was carried out in a seasoning solution, prepared with 4 kg of the additive, to obtain "BETTARA-ZUKE".

The product is moderately sweet, and excellent in color, brightness, flavor and biting properties. Also, the product is stable over a long period of storage to its low susceptibility to excessive fermentation.

EXAMPLE 17

Tablet

Fifty parts of acetyle-salicylic acid, 14 parts of crystalline mixture solid in powder form, obtained similarly as in EXAMPLE 3, and 4 parts of corn starch powder were mixed and kneaded sufficiently. Then, the mixture was tabletted, 5.25 mm thick and 680 mg, using a conventional tabletting machine.

The product is very moisture-resistant, and its physical strength is extremely high as well as being readily soluble in water.

EXAMPLE 18

Polyether Derivative of Maltitol

Three parts of anhydrous crystals of maltitol, obtained similarly as in EXAMPLE 2, and 0.2 parts of pyridine were placed together in a reaction vessel. The mixture was added with 3 parts of dimethyl sulfoxide, and propylene oxide gas was then charged therein, while keeping the reaction temperature at 90°–100° C. The reaction was suspended when about five parts of propylene oxide was consumed.

The solvents and residual reagent were removed by distillation at 120° C. and a reduced pressure of about 10–20 mmHg under nitrogen atmosphere. The residue was cooled to about 60° C., added gradually with about 5 parts of conc. hydrochloric acid with stirring, and further added with 5 parts of benzene to form salts which were taken then removed by filtration in vacuo. All benene, water and hydrochloric acid were removed from the filtrate by distillation to obtain about 8 parts of viscous oily polyether derivative of maltitol.

The derivative exhibits an excellent surface-active action: thus, it is favorably usable in various uses, such as emulsifier, thickener or moisture-retaining agent, as well as surface-active agent for general uses.

In addition to the above described uses, it is favorably usable as a material in polyurethane production using isocyanate compounds.

EXAMPLE 19

Fatty Acid Ester Derivative of Maltitol

Two parts of crystalline mixture solid in powder form, obtained similarly as in EXAMPLE 3, was dissolved in 7 parts of dimethyl formamide. To the solution was added 0.6 parts of methyl palmitate and 0.04 parts of potassium carbonate, and the mixture was subjected to ester-exchange reaction overnight at a pressure of about 100–200 mmHg and a temperature of about 80°–100° C. with sufficient stirring.

After completion of the reaction, the solvent was removed by distillation in vacuo, and the residue was washed twice with three parts of acetone. After concentration of the residue, the concentrate was washed with benzene and petroleum ether. The viscous oily product was immersed in three parts of acetone while heating, and the extract was allowed to stand under ice-chilling conditions, obtaining a precipitate which was then treated with acetone, and dried to obtain 0.6 parts of maltitol mono-palmitate.

The derivative exhibits a satisfactory surface-active action; thus, it is favorably usable as an emulsifier for foods as well as an ingredient fo detergents.

What we claim is:

1. In a process for the production of a shaped body containing solid maltitol comprising molding the ingredients into the desired shape, the improvement whereby the shaped body has no hygroscopicity attributable to the maltitol, wherein said solid maltitol is selected from the group consisting of anhydrous crystals of maltitol and a whole crystalline hydrogenated starch hydrolysate mixture solid containing anhydrous crystals of maltitol.

2. A process in accordance with claims 1, wherein said maltitol is in granular form and said molding step comprises slightly moistening said granular maltitol and molding to the desired shape under a slightly elevated pressure.

3. A process in accordance with claim 1, wherein said shaped body also contains at least one additional sweetener.

4. A process in accordance with claim 3, wherein said shaped body is in the form of a tablet.

5. A process in accordance with claim 2, wherein the ingredients of said shaped body consist essentially of said maltitol.

6. A process in accordance with claim 5, wherein said shaped body is in the shape of a fish, animal, cube or flower.

* * * * *